United States Patent [19]

Agaskar et al.

[11] Patent Number: 5,563,314

[45] Date of Patent: *Oct. 8, 1996

[54] PROCESS FOR THE CATALYTIC DEHYDROGENATION OF ALKANES TO ALKENES WITH SIMULTANEOUS COMBUSTION OF HYDROGEN

[76] Inventors: Pradyot A. Agaskar, 41 Navesink Dr., Hopewell, N.J. 08638; Robert K. Grasselli, 12 Black Rock Rd., Chadds Ford, Pa. 19317-9270; James N. Michaels, 804 Devon La., Neshanic Station, N.J. 08853; P. Thomas Reischman, 215 Rock Rd. West, Lambertville, N.J. 08530; David L. Stern, 2411 Town Ct. N., Lawrenceville, N.J. 08648; John G. Tsikoyiannis, 191 Snowden La., Princeton, N.J. 08540

[*] Notice: The term of this patent shall not extend beyond the expiration date of Pat. No. 5,430,209.

[21] Appl. No.: 423,626

[22] Filed: May 25, 1995

Related U.S. Application Data

[63] Continuation-in-part of Ser. No. 112,287, Aug. 27, 1993, Pat. No. 5,430,209.

[51] Int. Cl.⁶ ............... C07C 1/00; C07C 5/327
[52] U.S. Cl. ............. 585/654; 585/315; 585/662; 585/663
[58] Field of Search .................. 585/324, 656, 585/658, 661–663, 659, 315

[56] References Cited

U.S. PATENT DOCUMENTS

| | | | |
|---|---|---|---|
| 3,501,547 | 3/1970 | Nolan et al. | 260/680 |
| 3,937,748 | 2/1976 | Miklas | 260/683.3 |
| 4,739,124 | 4/1988 | Ward | 585/658 |
| 4,769,509 | 9/1988 | Josefowicz | 585/656 |
| 4,806,624 | 2/1989 | Herber et al. | 585/440 |
| 4,827,066 | 5/1989 | Herber et al. | 585/319 |
| 4,886,931 | 12/1989 | Bartek et al. | 585/656 |
| 4,921,828 | 5/1990 | Brazdil et al. | 502/205 |
| 4,940,826 | 7/1990 | Friede et al. | 585/600 |
| 4,990,714 | 2/1991 | Nemet-Mavrodin | 585/407 |
| 5,001,291 | 3/1991 | Holt et al. | 585/324 |
| 5,071,814 | 12/1991 | Saski et al. | 502/205 |
| 5,086,032 | 2/1992 | Mazzocchia et al. | 502/315 |
| 5,430,209 | 7/1995 | Agaskar et al. | 585/324 |
| 5,430,210 | 7/1995 | Grasselli et al. | 585/324 |

OTHER PUBLICATIONS

Shu, J. et al., "Centre de Recherche sur les Proprietes des Interfaces et la Catalyse (Cerpic)," Canadian Journal of Chemical Engineering, 69, 1036–1060 (1991).

Ziaka, Z. D. et al., "A high temperature catalytic membrane reactor for propane dehydrogenation," Journal of Membrane Science, 77, 221–232 (1993).

*Primary Examiner*—Glenn A. Caldarola
*Attorney, Agent, or Firm*—Ronald A. Bleeker; Peter W. Roberts

[57] ABSTRACT

There is provided a process for the net catalytic oxidative dehydrogenation of alkanes to produce alkenes. The process involves simultaneous equilibrium dehydrogenation of alkanes to alkenes and combustion of the hydrogen formed to drive the equilibrium dehydrogenation reaction further to the product alkenes. In the present reaction, the alkane feed is dehydrogenated over an equilbrium dehydrogenation catalyst in a first reactor, and the effluent from the first reactor is then passed into a second reactor containing a reducible metal oxide which serves to selectively combust hydrogen in an oxidation/reduction (REDOX) reaction. This particular mode of operation is termed a separate reactor, REDOX mode.

20 Claims, 3 Drawing Sheets

PROCESS FOR THE CATALYTIC DEHYDROGENATION OF ALKANES TO ALKENES WITH SIMULTANEOUS COMBUSTION OF HYDROGEN

CROSS-REFERENCE TO RELATED APPLICATION

This application is a continuation-in-part of U.S. application Ser. No. 08/112,287, filed Aug. 27, 1993, now U.S. Pat. No. 5,430,209.

BACKGROUND

There is provided a process for the net catalytic oxidative dehydrogenation of alkanes to produce alkenes. The process involves simultaneous equilibrium dehydrogenation of alkanes to alkenes and combustion of the hydrogen formed to drive the equilibrium dehydrogenation reaction further to the product alkenes.

Developments in zeolite catalysts and hydrocarbon conversion processes have created interest in utilizing light aliphatic feedstocks for producing $C_5+$ gasoline, diesel fuel, etc. In addition to chemical reactions promoted by medium-pore zeolite catalysts, a number of discoveries have contributed to the development of new industrial processes. These are safe, environmentally acceptable processes for utilizing aliphatic feedstocks. Conversions of $C_2$–$C_4$ alkenes and alkanes to produce aromatics-rich liquid hydrocarbon products were found by Cattanach (U.S. Pat. No. 3,760,024) and Yan et al. (U.S. Pat. No. 3,845,150) to be effective processes using the zeolite catalysts. In U.S. Pat. Nos. 3,960,978 and 4,021,502, Plank, Rosinski and Givens disclose conversion of $C_2$–$C_5$ olefins, alone or in admixture with paraffinic components, into higher hydrocarbons over crystalline zeolites having controlled acidity. Garwood et al. have also contributed to the understanding of catalytic olefin upgrading techniques and improved processes as in U.S. Pat. Nos. 4,150,062; 4,211,640; and 4,227,992. The above-identified disclosures are incorporated herein by reference.

Catalytic dehydrogenation and aromatization of light paraffinic streams, e.g., $C_2$–$C_4$ paraffins, commonly referred to as LPG, is strongly endothermic and typically carried out at temperatures between 540° and 820° C. (1000° and 1500° F.), the problem of transferring sufficient heat to a catalytic reaction zone to carry out the paraffin upgrading reaction remains as an obstacle to commercialization of these processes.

Dehydrogenation of paraffins to olefins has recently generated increasing interest as the market value of olefinic intermediate feedstocks continues to rise. Light olefins, particularly $C_2$–$C_4$ olefins, enjoy strong demand as building blocks for a wide range of valuable end products including fuels and specialized lubricants as well as thermoplastics.

Methods for supplying heat to an endothermic reaction zone include indirect heat exchange as well as direct heat exchange. Indirect heat exchange is exemplified by a multi-bed reactor with inter-bed heating or a fluid bed reactor with heat exchange coils positioned within the catalyst bed. Direct heat exchange techniques include circulation of inert or catalytically active particles from a high temperature heat source to the reaction zone, or the coupling of a secondary exothermic reaction with the primary endothermic reaction in a single catalytic reaction zone. Examples of such secondary exothermic reactions include (1) oxidative dehydrogenation of a portion of the feedstream, (2) sacrificial co-combustion of a part of the alkane/alkene mixture, and (3) combustion of carbonized species (e.g., coke) on the catalyst.

Currently known techniques for oxidative dehydrogenation are unfortunately not selective enough to achieve sufficiently high levels to allow for commercial practice and at least a part of the valuable product is over-oxidized, usually to the waste products, CO, $CO_2$, and $H_2O$.

Examples of such sacrificial co-combustion processes include those described in U.S. Pat. No. 3,136,713 to Miale et al. which teaches a method for heating a reaction zone by selectively burning a portion of a combustible feedstream in a reaction zone. Heat is directly transferred from the exothermic oxidation reaction to supply the endothermic heat for the desired conversion reaction.

A process for the oxidative dehydrogenation of propane is described in U.S. Pat. No. 5,086,032 to Mazzocchia et al.

Heat balanced reactions are also taught in U.S. Pat. Nos. 3,254,023 and 3,267,023 to Miale et al. Additionally, U.S. Pat. No. 3,845,150 to Yan and Zahner teaches a heat balanced process for the aromatization of hydrocarbon streams by combining the exothermic aromatization of light olefins with the endothermic aromatization of saturated hydrocarbons in the presence of a medium-pore zeolite catalyst.

Turning now to chemical reaction thermodynamics, it is well recognized that the extent of reaction may be increased by removing reaction products from contact with the reactants as the reaction products are formed. This principle finds application in U.S. Pat. No. 3,450,500 to Setzer et al. which teaches a process for reforming hydrocarbon feedstocks and withdrawing the hydrogen product from contact with the feedstock driving the equilibrium to favor increased hydrogen production. Articles by Shu et al. and by Ziaka et al. teach that the extent of reaction for equilibrium dehydrogenation reactions may be further driven to product olefin by the concomitant removal of the hydrogen formed with hydrogen selective membranes. The article by Shu et al. appears in the *Canadian Journal of Chemical Engineering*, 69, 1036–1060 (1991); and the article by Ziaka et al. entitled "A High Temperature Catalytic Membrane Reactor for Propane Dehydrogenation" appears in the *Journal of Membrane Science*, 77, 221–232 (1993).

Similarly, British Patent Application GB 2190397A describes a process for producing aromatic hydrocarbons by catalytic paraffin dehydrocyclodimerization. The process upgrades $C_2$–$C_6$ paraffins, i.e., ethane, propane, butane or a mixture thereof to a mixture of aromatic hydrocarbons and hydrogen by-product in a reactor provided with a membrane capable of selective, in-situ transfer of at least a portion of the hydrogen in the mixture across the membrane. Catalysts useful in the paraffin upgrading process are said to include zeolites, and in particular gallium-containing zeolites.

It is believed that the paraffin dehydrogenation reaction is equilibrium limited when carried out in a conventional reactor due to the thermodynamics of equilibrium dehydrogenation. For example, at 550° C. the equilibrium propylene from propane dehydrogenation, irrespective of catalyst, is limited to 33%. Thus, the state of the art of endothermic hydrogen-producing paraffin upgrading processes would clearly be advanced by a process and apparatus for increasing the extent of reaction while also providing a high temperature heat source to supply at least a portion of the endothermic heat of reaction.

SUMMARY

There is provided a process for converting an alkane of the formula, $C_nH_{2n+2}$, to an alkene of the formula, $C_nH_{2n}$, where n is the same for said alkane and said alkene and n is from 2 to 5, said process comprising the steps of:

(a) contacting said alkane with a solid material comprising a dehydrogenation catalyst under conditions sufficient to produce said alkene and $H_2$, wherein said dehydrogenation catalyst comprises at least one metal selected from the group consisting of Cr, Mo, Ga, Zn, and a Group VIII metal;

(b) contacting the effluent from step (a) with a reducible metal oxide under conditions sufficient to selectively convert said $H_2$ and reducible metal oxide to a reduced form of the metal oxide and water, wherein said reducible metal oxide is an oxide of at least one metal selected from the group consisting of Bi, In, Sb, Zn, Tl, Pb, and Te; and (c) contacting at least a portion of the effluent of step (b) with a solid material comprising a dehydrogenation catalyst under conditions sufficient to convert unreacted alkane to additional quantities of said alkene and $H_2$.

EMBODIMENTS

Alkanes are converted to olefins (and dienes) by an integrated process scheme which involves the direct equilibrium dehydrogenation of alkanes via known catalysts and the selective oxidation of the resulting hydrogen gas thus formed. The light paraffins which may be utilized for such reactions include $C_2$–$C_5$, such as propane and isobutane. As an illustrative example, the overall reaction scheme, demonstrated for propane oxidative dehydrogenation, is thus:

Scheme A:

Reaction 1 is documented in the literature and is known as propane equilibrium dehydrogenation. Butane and isobutane equilibrium dehydrogenation are also known and documented in the literature. Reaction 1 has been demonstrated to occur catalytically over $Cr/Al_2O_3$, $Mo/Al_2O_3$, iron-based catalysts, supported (supports include silica, alumina, zirconia, titania, and thoria) and unsupported noble metals (e.g., Pt, Pd, Rh, Ir, Ru, etc.), and supported and unsupported gallium and zinc oxides. Reaction 2 can proceed in the absence (redox mode), as opposed to the presence (cofed mode) of gaseous oxygen, over a number of reducible metal oxides. Catalyst 1 and $M_x{}^nO_y$ may be used together or in separate reactors.

Several recent, open literature reports have discussed the oxidative dehydrogenation of propane and butane to the corresponding olefins. These reactions are typically carried out by utilizing a mixture of alkane and oxygen cofed over a metal oxide catalyst. Typical operating temperatures are from 400° to 600° C., 1–5 atm. pressure, either with a diluent or in the absence of one.

The present invention differs from the system described above in that the reaction involves two separately functioning materials—an equilibrium dehydrogenation catalyst, and a solid oxide oxygen source for selective hydrogen combustion. These components may be used in separate reactors, connected in series or in a recycle mode, so as to drive the equilibration reaction (equation 1 above) further to the product side than is normally possible with only an equilibration catalyst. Thus, in the present scheme, the hydrogen would be combusted to $H_2O$ (or at least a portion of it), thus driving the equilibrium represented by equation 1 to the side of the products.

The catalyst used in the dehydrogenation reaction may be an equilibrium dehydrogenation catalyst comprising a Group VIII metal (i.e., Fe, Co, Ni, Ru, Rh, Pd, Os, Ir, or Pt). Of these Group VIII metals, the noble metals (i.e., Ru, Rh, Pd, Os, Ir, and Pt) are preferred. These Group VIII metals are preferably present in an at least partially reduced state with at least a portion thereof being in the free metal (i.e., zero valent) form. Examples of such equilibrium dehydrogenation catalysts include Pt, Pd, or other Group VIII metals either in bulk phase or supported on oxide supports (alumina, silica, titania, zirconia, zinc aluminate, etc.).

A particular dehydrogenation catalyst, which may be used in the present dehydrogenation reaction is a Pt/Sn/ZSM-5 catalyst, especially as described in U.S. Pat. Nos. 4,990,710 and 5,192,728. Such Pt/Sn/ZSM-5 catalysts may comprise 0.1 to 20 weight percent platinum and 0.1 to 20 weight percent tin with the remainder being ZSM-5. The ZSM-5 in this catalyst is essentially non-acidic and may comprise less than 0.1 weight percent of aluminum.

By means of the present invention, whereby hydrogen is selectively oxidized after being produced in the dehydrogenation of an alkane, it is possible to obtain greater than equilibrium yields of alkenes from the overall process. The following table provides thermodynamic calculations of equilibrium yields of propylene, butene, and isobutene from propane, n-butane, and i-butane, respectively.

| Temperature, °C. | Propane | n-Butane | i-Butane |
|---|---|---|---|
| 350 | 2 | 3 | 4 |
| 400 | 4 | 7 | 8 |
| 450 | 9 | 15 | 18 |
| 500 | 18 | 28 | 33 |
| 550 | 32 | 46 | 53 |
| 600 | 50 | 66 | 72 |
| 650 | 68 | 82 | 85 |
| 700 | 82 | 92 | 93 |

Figure 1:
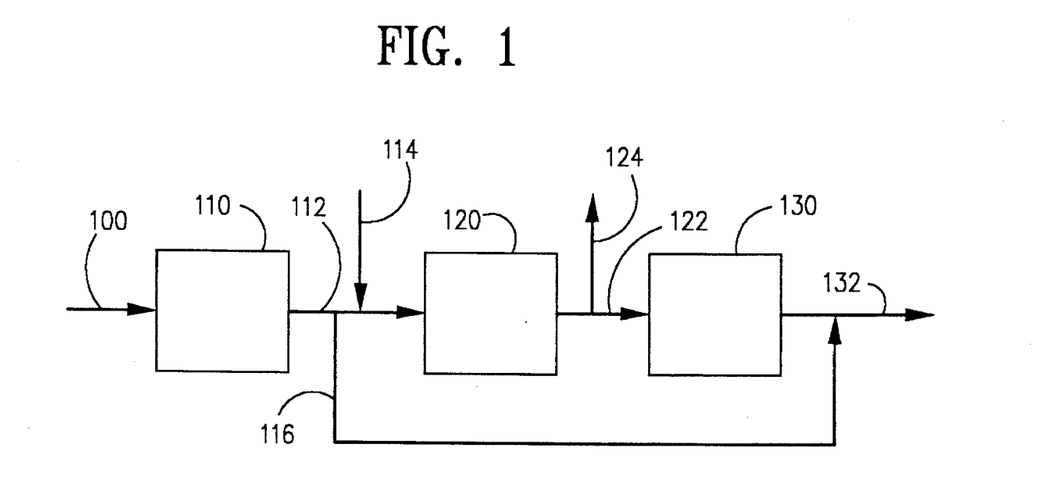
FIG. 1 provides a schematic diagram of an example of the present process, wherein a first dehydrogenation reactor is connected in series to an oxidation reactor which is, in turn, connected to a second dehydrogenation reactor.

FIG. 1 provides a schematic diagram of an example of the present process, wherein a first dehydrogenation reactor is connected in series to an oxidation reactor which is, in turn, connected to a second dehydrogenation reactor. In FIG. 1, a suitable alkane feed, such as propane, is introduced into dehydrogenation reactor 110 via line 100. The effluent from reactor 110, comprising alkene, hydrogen and unreacted alkane passes through line 112 to oxidation reactor 120, wherein hydrogen is selectively oxidized. The effluent from the oxidation reactor, comprising unreacted alkane, alkene and a reduced amount of hydrogen, then passes through a second dehydrogenation reactor 130, wherein unreacted alkane from the first dehydrogenation reactor is converted to additional alkene and hydrogen. The product from reactor 130 may be recovered via line 132 or it may be passed via line 132 to one or more oxidation reactors, each followed by a dehydrogenation reactor connected in series.

After the reducible metal oxide in the oxidation reactor is reduced to a point where it is ineffective for selectively oxidizing hydrogen, it may be regenerated. This regeneration involves shutting off the flow of alkane, alkene and hydrogen through line 112 and introducing oxygen, e.g., in the form of air, into reactor 120 via lines 114 and 112. Off gasses from the regeneration may be taken off by shutting off line 122 downstream of line 124 and opening line 124, so that off gasses pass through line 122 and out line 124.

The shut off of the flow of hydrocarbons and hydrogen to the oxidation reactor 120 during the regeneration cycle for reactor 120 may involve stopping the flow of alkane reactant to dehydrogen reactor 110 via line 100. Alternatively, however, the dehydrogenation reaction in reactor 110 may be allowed to continue during the regeneration cycle for reactor 120 by use of bypass line 116. More particularly, during the regeneration cycle for reactor 120, line 112 may be shut off at a point between lines 116 and 114 and bypass line 116 may be opened, thereby permitting the effluent from dehydrogenation reactor 110 to bypass oxidation reactor 120 and dehydrogenation reactor 130 and to pass directly to line 132. If line 132 is connected to an additional series of oxidation and dehydrogenation reactors, it would be possible to individually take sections of the overall series reactors out of service for the purposes of regenerating individual oxidation reactors at varying time intervals, thereby allowing the overall conversion of alkane to alkene to proceed on a substantially continuous basis.

Figure 2:
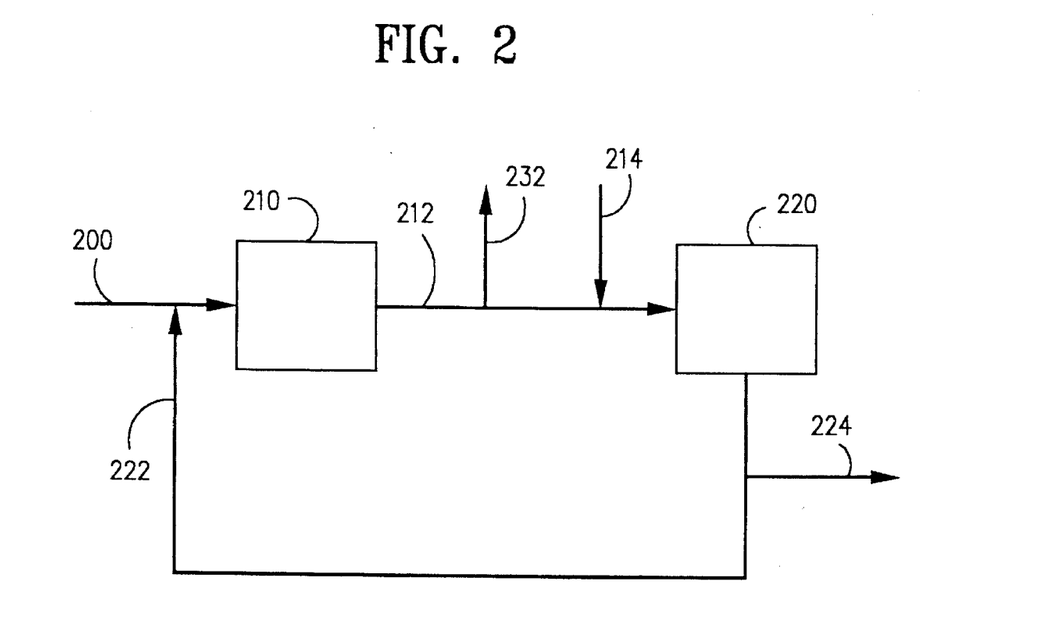
FIG. 2 provides a schematic diagram of an example of the present process, wherein a dehydrogenation reactor is connected to an oxidation reactor in a manner which facilitates recycle of the effluent from the oxidation reactor back into the dehydrogenation reactor.

FIG. 2 provides a schematic diagram of an example of the present process, wherein a dehydrogenation reactor is connected to an oxidation reactor in a manner which facilitates recycle of the effluent from the oxidation reactor back into the dehydrogenation reactor. In FIG. 2, a suitable alkane feed, such as propane, is introduced into dehydrogenation reactor 210 via line 200. The effluent from reactor 210, comprising alkene, hydrogen and unreacted alkane, passes through line 212 to oxidation reactor 220, wherein hydrogen is selectively oxidized. The effluent from the oxidation reactor, comprising unreacted alkane, alkene and a reduced amount of hydrogen, then passes through recycle line 222 to line 200 and back into dehydrogenation reactor 210, wherein unreacted alkane from the first dehydrogenation reactor pass is converted to additional alkene and hydrogen. The number of passes or recycle steps through the system depends on the desired level of alkane conversion to alkene product. When a sufficient level of conversion is achieved, the product may be recovered via line 232 or it may be passed via line 232 to a series of one or more additional oxidation and dehydrogenation reactors.

The recycle reaction scheme shown in FIG. 2 may be operated in a batch or continuous mode. In the batch mode, the flow of fresh alkane feed to reactor 210 via line 200 is shut off at a certain point in time so that the recycle stream from line 222 becomes the only source of reactant in reactor 210. While this batch mode recycle reaction is taking place, line 232 remains closed. After a desired level of conversion is achieved, line 232 may be opened and product recovered. The introduction of a flush gas, such as nitrogen, into the system, e.g., via line 214, may facilitate recovery of the product.

In a continuous mode, line 232 may be partially opened so that a metered amount of product is withdrawn, while the remainder of the effluent from reactor 210 passes into the oxidation reactor 220 via line 212. As a portion of the product is being continuously withdrawn via line 232, a corresponding amount of fresh alkane feed is introduced into reactor 210 along with the recycle stream.

After the reducible metal oxide in the oxidation reactor is reduced to a point where it is ineffective for selectively oxidizing hydrogen, it may be regenerated. This regeneration involves shutting off the flow of alkane, alkene and hydrogen through line 212 and introducing oxygen, e.g., in the form of air, into reactor 220 via lines 214 and 212. Off gasses from the regeneration may be taken off by shutting off line 222 downstream of line 224 and opening line 224, so that off gasses pass through line 222 and out line 224.

The shut off of the flow of hydrocarbons and hydrogen to the oxidation reactor 220 during the regeneration cycle for reactor 220 may involve stopping the flow of alkane reactant to dehydrogen reactor 210 via line 200. Alternatively, however, the dehydrogenation reaction in reactor 210 may be allowed to continue during the regeneration cycle for reactor 220 by using line 232 to bypass reactor 220. More particularly, during the regeneration cycle for reactor 220, line 212 may be shut off at a point between lines 232 and 214 and line 232 may be opened, thereby permitting the effluent from dehydrogenation reactor 210 to bypass oxidation reactor 220. If line 232 is connected to an additional series of oxidation and dehydrogenation reactors, it would be possible to individually take sections of the overall series reactors out of service for the purposes of regenerating individual oxidation reactors at varying time intervals, thereby allowing the overall conversion of alkane to alkene to proceed on a substantially continuous basis.

Figure 3:
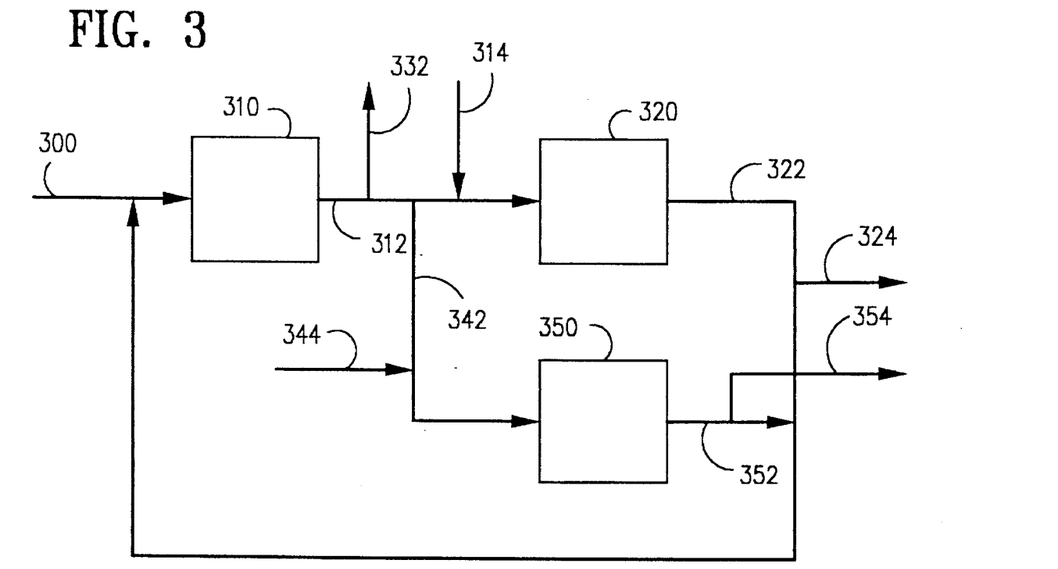
FIG. 3 provides a schematic diagram of an example of the present process, wherein a dehydrogenation reactor is connected to two oxidation reactors in a manner which facilitates a recycle mode of operation, while permitting one oxidation reactor to be regenerated as the other oxidation reactor is being used to selectively oxidize hydrogen in the effluent from the dehydrogenation reactor.

FIG. 3 provides a schematic diagram of an example of the present process, wherein a dehydrogenation reactor is connected to two oxidation reactors in a manner which facilitates a recycle mode of operation, while permitting one oxidation reactor to be regenerated as the other oxidation reactor is being used to selectively oxidize hydrogen in the effluent from the dehydrogenation reactor. In FIG. 3, a suitable alkane feed, such as propane, is introduced into dehydrogenation reactor 310 via line 300. The effluent from reactor 310, comprising alkene, hydrogen and unreacted alkane, first passes through line 312 to a first oxidation reactor 320, wherein hydrogen is selectively oxidized. In this initial phase of the operation, line 342 to the second oxidation reactor is closed, thereby preventing the flow of effluent from dehydrogenation reactor 310 to the second oxidation reactor 350. The effluent from the first oxidation reactor 320, comprising unreacted alkane, alkene and a reduced amount of hydrogen, then passes through recycle line 322 to line 300 and back into dehydrogenation reactor 310, wherein unreacted alkane from the first dehydrogenation reactor pass is converted to additional alkene and hydrogen. The number of passes or recycle steps through the system depends on the desired level of alkane conversion to alkene product. When a sufficient level of conversion is achieved, the product may be recovered via line 332 or it may be passed via line 332 to a series of one or more additional oxidation and dehydrogenation reactors.

After the reducible metal oxide in the first oxidation reactor 320 is reduced to a point where it is ineffective for selectively oxidizing hydrogen, it may be regenerated. This regeneration involves shutting off the flow of alkane, alkene and hydrogen through line 312 by shutting line 312 at a point between lines 342 and 314 and introducing oxygen, e.g., in the form of air, into reactor 320 via line 314. Off gasses from the regeneration may be taken off by shutting off line 322 at a point between lines 324 and 352 and opening line 324, so that off gasses pass through line 322 and out line 324.

As the flow of effluent from dehydrogenation reactor 310 to the first oxidation reactor is being shut off, the flow of this effluent to the second oxidation reactor 350 may be started by opening line 342 and allowing the effluent to pass through line 342 into the second oxidation reactor 350. The effluent from the second oxidation reactor 350 then passes through line 352 to recycle line 322 to line 300 and back into dehydrogenation reactor 310.

After the first oxidation reactor 320 has been regenerated, and the reducible metal oxide in the second oxidation reactor is spent, the flow of effluent from the dehydrogenation reactor 310 may be rerouted to the first oxidation reactor 320, and the second oxidation reactor 350 may be regenerated by closing line 342 at a point between lines 312 and 344, closing line 352 at a point between lines 354 and 322, opening lines 344 and 354, passing oxygen via lines 344 and 342 into the second oxidation reactor 350, and removing off gasses via lines 352 and 354.

The reaction scheme in FIG. 3 may be operated in a batch or continuous mode in a manner analogous to that described hereinabove in connection with FIG. 2.

As described in the Examples below, particularly selective combustion of hydrogen over alkanes or alkenes is not a property common to all reducible metal oxides but rather is limited over a fairly narrow selection of metal oxides found to possess this particularly selective hydrogen combustion capability.

The reducible metal oxides, which are useful for promoting selective hydrogen combustion, must first have the property of being reducible under the present oxidation conditions so as to provide a source of oxygen to combust $H_2$. Accordingly, essentially nonreducible, essentially inert oxides, such as silica, would not fit this first criteria. A second criteria, which the present reducible oxide must fit, is that it provides oxygen in a selective manner, whereby it selectively causes $H_2$ to be converted to $H_2O$ without also oxidizing substantial quantities of the hydrocarbons (i.e., alkanes and alkenes) present. An example of such a nonselective reducible metal oxide, which tends to oxidize substantial quantities of hydrocarbons is vanadium oxide.

As is shown in Examples below, the oxides of bismuth are particularly selective for hydrogen combustion over hydrocarbon combustion, while the oxides of vanadium are not.

The reducible metal oxides, which are particularly selective for the present selective hydrogen combustion reaction, contain certain metals selected from a narrow quadrant of the periodic table, i.e., the upper right hand corner thereof. These metals include Bi, In, Sb, Zn, Tl, Pb, and Te. A review of the periodic table suggests that this group of elements is centered by the location of the particular elements, Bi, In, and Sb.

In addition to the reducible metal oxide, the solid oxygen source may include other components such as supports for the reducible metal oxide. Examples of such supports include nonreducible, essentially inert oxides, such as silica, alumina, zirconia, titania, hafnia, and mixtures of these oxides, such as silica/alumina. Other optional components of the present solid oxygen source include certain elements, particularly in oxide form, which have been used as promoters for known oxidation or oxidative dehydrogenation catalysts. Particular examples of oxides, which may be optionally included in the present solid oxygen source, include one or more oxides of elements selected from the group consisting of Mo, W, P, and La. Although the question of whether such oxides of Mo, W, P, and La actually have a beneficial or promoting effect in the present selective hydrogen combustion reaction has been largely unexplored, it is at least believed that these particular oxides do not have a detrimental effect.

Although oxides of Mo, W, P, and La, as well as oxides of Si, Al, Zr, Ti, and Hf, need not be avoided in the present solid oxygen source, other oxides, which tend to promote the oxidation of alkanes and alkenes, should be avoided. Examples of such oxides, which are preferably not included in the present solid oxygen sources, include oxides of one or more of the following elements: V, Fe, Cu, Nb, and Ta.

The solid oxygen source may contain, for example, at least 1 wt. % of reducible metal oxide. Elemental analysis of the solid oxygen source may reveal the presence of, for example, at least 0.5 wt. % of one or a combination of metals selected from the group consisting of Bi, In, Sb, Zn, Tl, Pb, and Te.

The solid oxygen source described herein may be an oxide of a single metal, such as bismuth or antimony, or it may be a mixed metal oxide. An example of a mixed metal oxide is a compound of the following empirical formula $$Bi_aSb_bTe_cA_dB_eC_fO_x$$

where
  A=P, La, Ce, Y, Ru, Co, Ni, Al, In, Ga, and/or Ge
  B=Mo, W, Cr, Sn, Nb, Ta, and/or Ti
  C=an alkali, an alkaline earth, Ag, and/or Tl
  O=oxygen
where
  a,b,c=0 to 12
  a+b+c>0
  d=0 to 12
  e=0 to 12
  f=0 to 12
  x=dictated by the oxidation states of the remaining elements.

Another example of a mixed metal oxide is a compound of the following empirical formula $$A_aB_bC_cD_dO_x$$

where
A=In, Cr, Al, Zn, Pb, and/or a Rare Earth (preferred RE=Tb, Gd, Ce, Y, and/or La)
B=La, Ce, Y, Ru, Fe, Co, Ni, Cu, Al, In, Ga, and/or Ge
C=P, Mo, W, Cr, Sn, Nb, Ta, and/or Ti
D=an alkali, an alkaline earth, Ag, and/or Tl
O=oxygen
where
0<a<12
b=0 to 12
c=0 to 12
d=0 to 12
e=0 to 12
x=dictated by the oxidation states of the remaining elements.

EXAMPLE 1

In this Example, it is demonstrated that some metal oxides can be reduced much faster by hydrogen than by hydrocarbons; hence, they exhibit superior selective hydrogen combustion (SHC) properties.

A gravimetric, Cahn balance apparatus was used to measure the reduction rates of several metal oxides with hydrogen and $C_3$ hydrocarbons at 500° C. These rates and the selectivity of the examined oxides for SHC are listed in Table 1.

In Table 1, MCC (multicomponent catalyst) stands for a compound of the formula $$Cs_{0.5}Ni_{2.5}Co_{4.5}Fe_3BiSbMo_{12}O_x,$$

where X is dictated by the oxidation states of the remaining elements. Also in Table 1, $[O]_L$ stands for lattice oxygen.

TABLE 1

Selectivities of SHC Catalysts at 500° C.
for the Removal of Lattice Oxygen to Convert
Hydrogen vs. Propane, Measured by Gravimetry

| Metal Oxide | Wt. % $[O]_L$ Removed In 5 min. by: Hydrogen | Wt. % $[O]_L$ Removed In 5 min. by: Propane | Hydrogen to form water[a] | Propane to form propylene, $CO_x$, and water[b] |
|---|---|---|---|---|
| $Bi_2Mo_3O_{12}$ | 10.2 | 0.10 | 99.0 | 1.0 |
| $In_2Mo_3O_{12}$ | 12.9 | 0.21 | 98.4 | 1.6 |
| $Al_2Mo_3O_{12}$ | 5.36 | 0.25 | 95.5 | 4.5 |
| $Bi_2O_3$ | 8.85 | 0.44 | 95.3 | 4.7 |
| $Fe_2Mo_3O_{12}$ | 3.32 | 0.21 | 94.0 | 6.0 |
| MCC | 8.6 | 0.95 | 90.1 | 9.9 |
| $Cr_2Mo_3O_{12}$ | 6.97 | 0.91 | 88.5 | 11.5 |
| $La_2Mo_3O_{12}$ | 1.02 | 0.17 | 85.7 | 14.3 |
| $Ce_2Mo_3O_{12}$ | 1.04 | 0.27 | 79.4 | 20.6 |
| $MoO_3$ | 1.0 | 0.28 | 78.1 | 21.9 |
| $V_2O_5$ | 0.9 | 13.6 | 6.2 | 93.8 |

[a] % selectivity for $H_2 = \dfrac{\text{wt. \% }[O]_L \text{ removed by } H_2}{\text{wt. \% }[O]_L \text{ removed by } H_2 + \text{wt. \% }[O]_L \text{ removed by } C_3°}$

[b] % selectivity for $C_3° = \dfrac{\text{wt. \% }[O]_L \text{ removed by } C_3°}{\text{wt. \% }[O]_L \text{ removed by } C_3° + \text{wt. \% }[O]_L \text{ removed by } H_2}$ Table 1 shows that $Bi_2O_3$; indium, bismuth, lanthanum, cerium, and aluminum molybdates; and MCC exhibit the highest selectivities for hydrogen combustion in the presence of propane, while $V_2O_5$ exhibits the lowest.

EXAMPLE 2

An equimolar mixture of 15% hydrogen and 15% propylene in helium was passed over 1 g of 42% $Bi_2O_3$/58% $SiO_2$ at a total flowrate of 170 cc/min at 550° C. for 140 seconds. The product gas was collected and analyzed with gas chromatography. $H_2$ conversion to $H_2O$ was greater than 85%, while the conversion of propylene was less than 0.5%.

EXAMPLE 3

The same experiment was conducted as in Example 2, except that the feed was flowed over the sample for 600 seconds at a total flowrate of 40 cc/min. The $H_2$ conversion in the reactor effluent was 79%, while the conversion of propylene was approximately 1%.

EXAMPLE 4

An equimolar mixture of 15% hydrogen and 15% propane in helium was passed over 1 g of 50% $V_2O_5$/50% $Al_2O_3$ at a total flowrate of 170 cc/min at 550° C. for 140 seconds. The product gas was collected and analyzed with gas chromatography. $H_2$ conversion to $H_2O$ was 81%, while the conversion of propane, mostly to CO, $CO_2$, and $H_2O$, was 23%.

EXAMPLE 5

The same experiment was conducted as in Example 4, except that the feed was flowed over the sample for 600 seconds at a total flowrate of 40 cc/min. The $H_2$ conversion in the reactor effluent was only 11%, while the conversion of propane to waste products was 24%. Examples 4 and 5 illustrate that, in sharp contrast to $Bi_2O_3$, $V_2O_5$ does not exhibit SHC properties, since its lattice oxygen is particularly active for the conversion of hydrocarbons.

EXAMPLE 6

Figure 4:
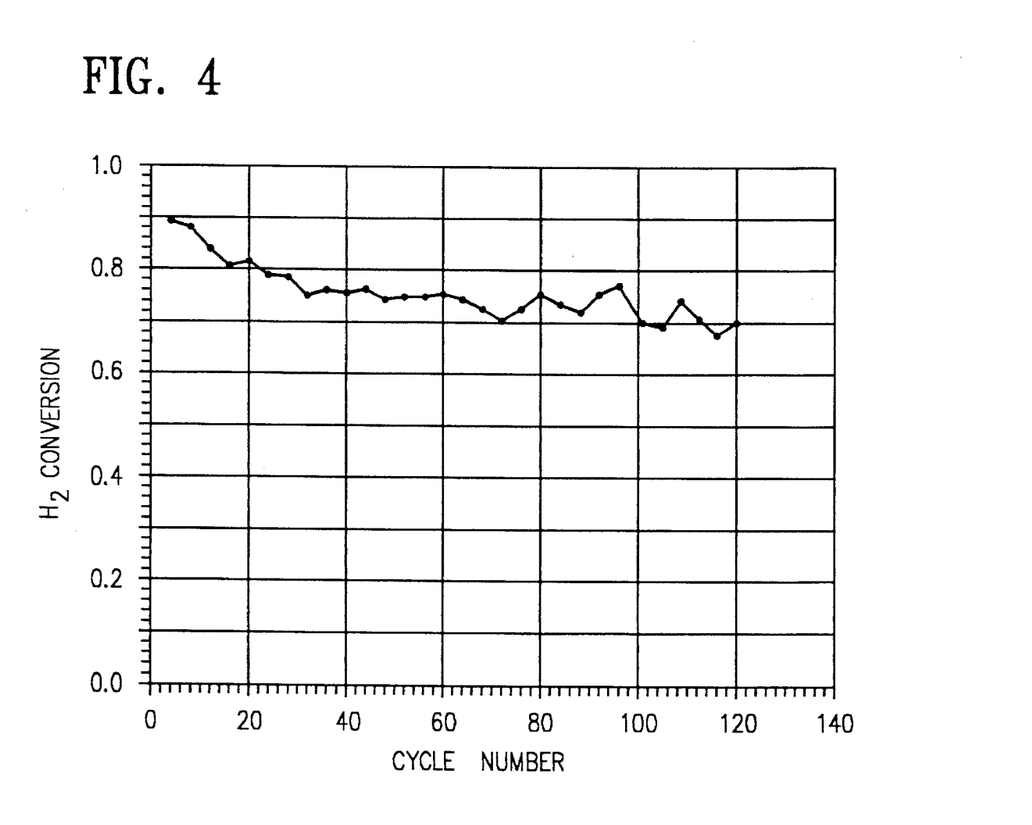
FIG. 4 is a graph showing conversion of $H_2$ and propylene over $Bi_2O_3/SiO_2$ during the course of 120 REDOX cycles.

The same material as in Examples 2 and 3 was exposed to 120 consecutive redox cycles. A redox cycle consists of an oxidation phase (flow of excess air for 5 minutes) followed by a reduction phase (flow of 15% $H_2$, 15% $C_3$= at 170 cc/min for 140 seconds). The oxidation and reduction phases are separated by two helium purge phases. The $H_2$ conversion as a function of cycle number is shown in FIG. 4. The conversion of propylene was negligibly small (less that 0.5%), mostly to $CO_2$. The conversion of $H_2$ is attributed to its oxidation to $H_2O$ by the lattice oxygen of $Bi_2O_3$ which did not oxidize virtually any of the hydrocarbon present.

EXAMPLE 7

In this Example, it is demonstrated that $Bi_2O_3$ is selective for combustion of $H_2$ in the presence of hydrocarbons and also in the presence of cofed gaseous oxygen.

Figure 5:
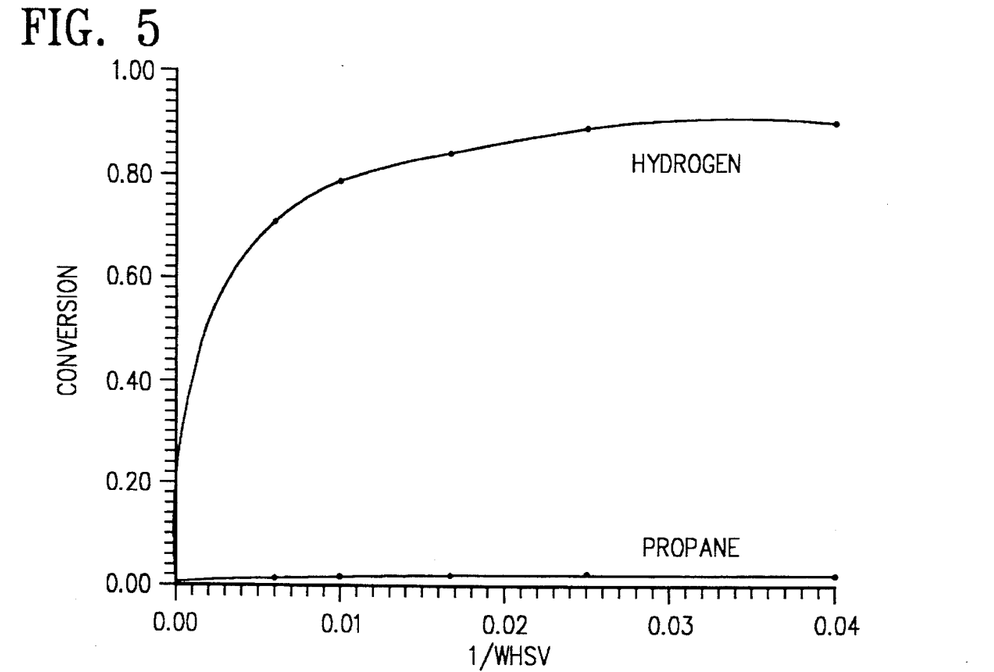
FIG. 5 is a graph showing conversions of hydrogen and propane as a function of residence time in a reactor.

The activity and selectivity of $Bi_2O_3$ in the cofed mode was examined using equimolar $H_2$-$C_3$° and $H_2$-$C_3$= mixtures, with stoichiometric amounts of gaseous oxygen (15% $C_3$°, 15% $H_2$, 7.5% $O_2$). Shown in FIG. 5 are the conversions of hydrogen and propane at 500° C. as a function of residence time. The propane conversion, mostly to $CO_2$, was always less than 2%, while the conversion of hydrogen exceeded 90% at high residence time. This indicates that the deliberately limited supply of cofed oxygen had been utilized very selectively to preferentially activate the hydrogen gas.

Figure 6:
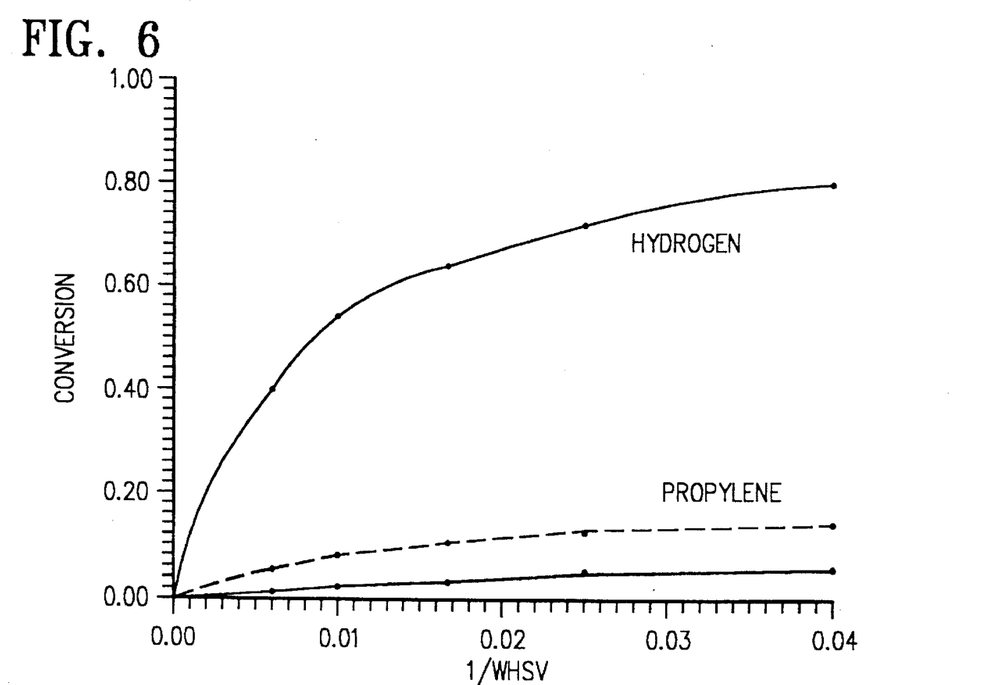
FIG. 6 is a graph showing conversions of hydrogen and propylene as a function of residence time in a reactor.

Shown in FIG. 6 are the corresponding results with a hydrogen/propylene mixture at 450° C. The solid lines correspond to a 15% $C_3=$, 15% $H_2$, 7.5% $O_2$ feed. The dashed line is the propylene conversion obtained with a 15% $C_3=$, 0% $H_2$, 7.5% $O_2$ feed. The selectivity of $Bi_2O_3$ for hydrogen combustion in the presence of propylene is still high, although not as high as in the presence of propane. Furthermore, the propylene conversion is less when hydrogen is present.

EXAMPLE 8

A series of metal oxides were examined with the experiment described in Examples 2 and 3 to evaluate their SHC properties. These results of these experiments are summarized in the following table.

| Metal Oxide | Flowrate, cc/min | $H_2$Conv, % | $C_3 =$ Conv., % |
|---|---|---|---|
| Silica | 170 | 10 | <0.5 |
| | 40 | <10 | 1.5 |
| $Sb_2O_3/SiO_2$ | 170 | 40 | <0.5 |
| | 40 | 16 | 1.5 |
| $Bi_2O_3/SiO_2$ | 170 | >90 | <0.5 |
| | 40 | 80 | 1.2 |
| $Bi_9PW_{12}O_x$ | 170 | 55 | 1.5 |
| | 40 | 61 | 5.5 |
| $TbO_x/SiO_2$ | 170 | 16 | 1.0 |
| | 40 | 23 | 4.0 |
| $PbO_x/SiO_2$ | 170 | 16 | <0.5 |
| | 40 | <10 | 2.5 |
| $WO_3/SiO_2$ | 170 | 22 | <0.5 |
| | 40 | <10 | 3.8 |
| $ZnO_2/SiO_2$ | 170 | 20 | 0.8 |
| | 40 | 40 | 1.5 |
| $GdO_x/SiO_2$ | 170 | 10 | <0.5 |
| | 40 | <10 | 1.5 |
| $InO_x/SiO_2$ | 170 | 18 | 1.4 |
| | 40 | 25 | 2.5 |
| $GaO_x/SiO_2$ | 170 | <10 | 6.0 |
| | 40 | <10 | 8.4 |
| $GeO_x/SiO_2$ | 170 | <10 | <0.5 |
| | 40 | <10 | <1.0 |

EXAMPLE 9

In this Example, it is illustrated that higher than equilibrium propylene yields from propane can be obtained by using physical mixtures of appropriate dehydrogenation catalysts with SHC metal oxides.

A physical mixture with equal weights of Pt-Sn-ZSM-5 (0.65% Pt) and 42% $Bi_2O_3$/58% $SiO_2$ was prepared by combining pelleted, 20–40 mesh size particles of the two materials. This mixture was compared to Pt-Sn-ZSM-5 for the dehydrogenation of propane to propylene at 540° C. and 1 atm total pressure. A gas stream of pure propane was passed over 2 g of the mixed catalyst system at a flowrate of 17 cc/min for 166 sec. The reactor effluent was collected in an evacuated gas bulb and was analyzed. The same experiment was also conducted with 1 g Pt-Sn-ZSM-5. The product analysis in each case was as follows, wherein $C_3$ stands for propane, $C_3=$ stands for propylene, $CO_x$ stands for $CO+CO_2$ and $C_3^-$ stands for cracked products.

| Catalyst | $C_3$Conv. | $C_3 =$ Yield | $CO_x$Yield | $C_3^-$Yield |
|---|---|---|---|---|
| Pt—Sn—ZSM-5 | 24.2 | 22.1 | 0.6 | 1.5 |
| Mixture | 47.0 | 42.0 | 3.0 | 2.0 |

EXAMPLE 10

The same experiment as in Example 9 was conducted over the mixed catalyst system, except that feed was passed over the catalyst for 332 sec. Propane conversion was 42.8%; and propylene, $CO_x$, and cracked product yields were 38.8, 1.9, and 2.0%, respectively.

EXAMPLE 11

The same experiment as in Example 9 was conducted over the mixed catalyst system, except that feed was passed over the catalyst at a flowrate of 8.5 cc/min for 332 sec. Propane conversion was 47.8%; and propylene, $CO_x$, and cracked product yields were 39.7, 4.7, and 3.4%, respectively.

EXAMPLE 12

The same experiment as in Example 9 was conducted over a mixture of 2 g Pt-Sn-ZSM-5 and 1 g $Bi_2O_3/SiO_2$. Propane conversion in the collected product was 50.2%; and propylene, $CO_x$, and cracked product yields were 40.7, 4.6, and 4.9%, respectively.

EXAMPLE 13

1 g of Pt/Sn/ZSM-5 was mixed with 1 g of the metal oxide to be tested. The catalyst mixture was first calcined in air at 550° C. and the feed was 100% propane. The feed was passed over the catalyst mixture at 17 cc/min (corresponding to WHSV=2 g/gPt/Sn/ZSM5*hour) for 332 seconds. The reactor effluent was collected in an evacuated glass bulb and was analyzed. The propylene and COx yields obtained with each metal oxide are shown in Table 2 below. The base case experiment is with no metal oxide.

In Table 2, $C_3=$ sel. stands for $C_3=$ Yield divided by $C_3$ Conv.

| Catalyst | $C_3 =$ Yld | COxYld | $C_3$ Conv. | $C_3=$ sel |
|---|---|---|---|---|
| $Bi_2O_3/SiO_2$ | .308 | .017 | .325 | .948 |
| $BiLaOx/SiO_2$ | .301 | .022 | .323 | .932 |
| $BiSbOx/SiO_2$ | .260 | .010 | .270 | .963 |
| $Bi_2Mo_3O_{12}/SiO_2$ | .207 | .074 | .281 | .737 |
| $In_2Mo_3O_{12}/SiO_2$ | .334 | .020 | .354 | .944 |
| $In_2MoO_6/SiO_2$ | .237 | .009 | .246 | .963 |
| No Met. Oxide | .183 | .020 | .203 | .901 |
| $Al_2Mo_3O_{12}/SiO_2$ | .179 | .039 | .218 | .821 |
| $Cr_2Mo_3O_{12}/SiO_2$ | .181 | .046 | .227 | .797 |
| $MoO_3/SiO_2$ | .160 | .038 | .198 | .808 |
| $Fe_2O_3/SiO_2$ | .188 | .051 | .239 | .787 |
| $Nb_2O_5/SiO_2$ | .188 | .031 | .219 | .858 |
| $V_2O_5/SiO_2$ | .164 | .147 | .311 | .527 |

What is claimed is:
1. A process for converting an alkane of the formula,

$$C_nH_{2n+2},$$

to an alkene of the formula, $$C_nH_{2n},$$

where n is the same for said alkane and said alkene and n is from 2 to 5, said process comprising the steps of:

(a) contacting said alkane with a solid material comprising a dehydrogenation catalyst under conditions sufficient to produce said alkene and $H_2$, wherein said dehydrogenation catalyst comprises at least one metal selected from the group consisting of Cr, Mo, Ca, Zn, and a Group VIII metal;

(b) contacting the effluent from step (a) with a solid oxygen source comprising a reducible metal oxide under conditions sufficient to selectively convert said $H_2$ and reducible metal oxide to a reduced form of the metal oxide and water, wherein said reducible metal oxide is an oxide of at least one metal selected from the group consisting of Bi, In, Sb, Zn, Tl, Pb, and Te; and (c) contacting at least a portion of the effluent of step (b) with a solid material comprising a dehydrogenation catalyst under conditions sufficient to convert unreacted alkane to additional quantities of said alkene and $H_2$.

2. A process according to claim 1, wherein step (c) is accomplished by recycling effluent from the reaction zone of step (b) to the reaction zone of step (a).

3. A process according to claim 1, wherein step (c) is conducted in a reaction zone separate from the reaction zone of step (a).

4. A process according to claim 3, wherein the entire effluent from step (b) is used in step (c).

5. A process according to claim 1 further comprising the steps of:

(d) interrupting the reaction in the reaction zone of step (b);

(e) reacting the reduced form of the metal oxide with a source of oxygen under conditions sufficient to regenerate the original oxidized form of the reducible metal oxide; and (f) resuming the reaction in the second reaction zone using the regenerated form of the reducible metal oxide.

6. A process according to claim 5, wherein steps (d), (e), and (f) are conducted periodically.

7. A process according to claim 1, wherein said alkane is ethane.

8. A process according to claim 1, wherein said alkane is propane.

9. A process according to claim 1, wherein said alkane is isobutane and/or n-butane.

10. A process according to claim 5, wherein said dehydrogenation catalyst comprises platinum.

11. A process according to claim 1, wherein said reducible metal oxide comprises an oxide of indium.

12. A process according to claim 5, wherein said reducible metal oxide comprises $Bi_2O_3$.

13. A process according to claim 5, wherein said reducible metal oxide comprises a mixed metal oxide containing bismuth.

14. A process according to claim 5, wherein said reducible metal oxide comprises $Sb_2O_4$ or a mixed metal oxide containing antimony.

15. A process according to claim 5, wherein said reducible metal oxide comprises $Bi_aSb_bO_x$, where a and b are each greater than 0 and less than or equal to 12 and x is determined by the oxidation states of Bi and Sb under reaction conditions.

16. A process according to claim 1, wherein the dehydrogenation catalyst comprises platinum, and the reducible metal oxide contains bismuth, antimony, indium, or molybdenum, or a mixture thereof.

17. A process according to claim 1, wherein said solid oxygen source comprises a support selected from the group consisting of silica, alumina, zirconia, titania, hafnia, and mixtures thereof.

18. A process according to claim 1, wherein said solid oxygen source comprises one or more oxides of an element selected from the group consisting of Mo, W, P, and La.

19. A process according to claim 1, wherein said dehydrogenation catalyst and said solid oxygen source are discrete materials which do not share the same support.

20. A process according to claim 16, wherein said dehydrogenation catalyst comprises 0.1 to 20 weight percent platinum and 0.1 to 20 weight percent tin with the remainder of said dehydrogenation catalyst being ZSM-5.

* * * * *